United States Patent
Hu

(10) Patent No.: US 10,827,922 B2
(45) Date of Patent: Nov. 10, 2020

(54) APPARATUS AND METHOD FOR OBJECTIVE VISUAL ACUITY MEASUREMENT USING DYNAMIC VELOCITY THRESHOLD FILTER IN OPTOKINETIC RESPONSE PROCESSING

(71) Applicant: Zongqi Hu, Raritan, NJ (US)

(72) Inventor: Zongqi Hu, Raritan, NJ (US)

( * ) Notice: Subject to any disclaimer, the term of this patent is extended or adjusted under 35 U.S.C. 154(b) by 267 days.

(21) Appl. No.: 16/166,927

(22) Filed: Oct. 22, 2018

(65) Prior Publication Data

US 2020/0121184 A1    Apr. 23, 2020

(51) Int. Cl.
*A61B 3/14* (2006.01)
*A61B 3/10* (2006.01)
*A61B 3/113* (2006.01)
*A61B 3/02* (2006.01)
*A61B 5/00* (2006.01)
(Continued)

(52) U.S. Cl.
CPC .............. *A61B 3/113* (2013.01); *A61B 3/022* (2013.01); *A61B 3/024* (2013.01); *A61B 5/0496* (2013.01); *A61B 5/4863* (2013.01)

(58) Field of Classification Search
CPC ... A61B 5/4023; A61B 5/0022; A61B 5/4064; A61B 3/113; A61B 5/16; A61B 5/162; A61B 5/4076; A61B 5/6803; A61B 5/4082; A61B 5/4088; A61B 3/145; A61B 5/163; A61B 5/4094; A61B 5/4863; A61B 3/0041; A61B 3/032; A61B 3/112; A61B 5/1101; A61B 5/1124; A61B 5/121; A61B 2505/09; A61B 2562/0219; A61B 2562/0223; A61B 3/0025; A61B 3/0091; A61B 3/022; A61B 3/024; A61B 3/10; A61B 3/18; A61B 5/02055; A61B 5/0402; A61B 5/0476

USPC ........ 351/200, 205–206, 209–211, 221–223, 351/243–246
See application file for complete search history.

(56) References Cited

U.S. PATENT DOCUMENTS

| 4,634,243 A | 1/1987 | Massof et al. |
| 4,838,684 A | 6/1989 | Smith |

(Continued)

OTHER PUBLICATIONS

"Visual Evoked Potential Assessment of the Effects of Glaucoma on Visual Subsystems," Vision Research 38 (1998) pp. 1901-1911. Vivienne C. Greenstein, Steven Seliger, Vance Z.
(Continued)

*Primary Examiner* — Brandi N Thomas
(74) *Attorney, Agent, or Firm* — Walter J. Tencza, Jr.

(57) ABSTRACT

Optokinetic nystagmus (OKN) is an eye movement elicited by the tracking of moving objects in a visual field. It is characterized by an alternating smooth pursuit in one direction and saccadic movement in the other direction. The presence or absence of OKN indicates whether or not the moving stimulus was visible to the observer, without the explicit cooperation of the observer. It can be a tool for objective visual acuity assessment for patients such as young children who lack cognitive, attentional and language capabilities. Since the patient's head movement and unstable eye gaze may occur during the test, which often brings noises and irrelevant activities in the responses, making recognition of presence/absence of the OKN a challenging task. The present invention, using a dynamic velocity threshold (DVT) filter, provides a system and method for a quick and reliable OKN test and quantitative assessment of visual acuity.

16 Claims, 8 Drawing Sheets

(51) Int. Cl.
*A61B 5/0496* (2006.01)
*A61B 3/024* (2006.01)

(56) References Cited

U.S. PATENT DOCUMENTS

| | | | |
|---|---|---|---|
| 5,065,767 | A | 11/1991 | Maddess |
| 5,176,147 | A | 1/1993 | Bodis-Wollner |
| 5,295,495 | A | 3/1994 | Maddess |
| 5,539,482 | A | 7/1996 | James et al. |
| 5,912,723 | A | 6/1999 | Maddess |
| 6,477,407 | B1 | 11/2002 | Klistomer et al. |
| 6,527,391 | B1 | 3/2003 | Heljl et al. |
| 6,688,746 | B2 | 2/2004 | Malov |
| 7,396,128 | B2 | 7/2008 | Feher et al. |
| 8,382,286 | B2 | 2/2013 | Legerton |
| 2009/0018407 | A1* | 1/2009 | Jung .............. A61B 5/0022 600/301 |
| 2014/0171756 | A1 | 6/2014 | Waldorf |

OTHER PUBLICATIONS

Multifocal VEP and ganglion cell damage: Applications and limitations for the study of Glaucoma. Progress in Retinal and Eye Research, 22, pp. 201-251. Hood, D.C. & Greenstei.

Badr, A.A., Zemon, V.M., Greenstein, V.C., Clemens, C.J., Holopigian, K., Seiple, W.: M-versus P-Function: Relationship to visual field loss in patients with open angel glauco.

Benoff, K., Fitzerald, K. Zemon, V. Pinkhasov, E., Gordon, J., Cibis, G.: Magnocelluar ON-pathway deficits in Duchenne Muscular Dystrophy: A visual evoked potential study. In.

Fitzgerald, K.M., Hartmann, E.E., Zemon, V.M.: Pattern VEPs to cotnrast-increment and -decrement stimuli in patients with Duchenne Muscular Dystrophy or Congenitally Stationar.

"A new statistic for steady-state evoked potentials," Jonathan D. Victor and Joelle Mast, Publication Jul. 6, 1990, New York, NY, pp. 378-388.

Hartline, H.K.: The response of single optic nerve fibers of the vertebrate eye to illumination of the retina. American Journal of Physiology, 1938, 121, 400-415.

Kaplan, E., Lee, B.B., Shapley, R.M.: New views of primate retinal function. In: Progress in Retinal Research (Osborne, N.N. & Chader, G.J., eds), 1990, 9, 273-336. New York.

Joon Young Hyon, Hwan Eok Yeo, Jong-Mo Seo, In Bun Lee, Jeong-Min Hwang, Objective measurement of distance visual acuity determined by computerized optokinetic nystagmus test.

Nikki J. Rubinstein, Larry A. Abel, "Optokinetic nystagmus suppression as index of the Allocation of visual attention", Investigative Ophthalmology & Visual Science, Jan. 2.

Mehrdad Sani, Benjamin Thompson, Jason Turuwhenua, "An optokinetic nystagmus detection method for use with young children", IEEE Trans. Engineering in Health and Medicine, Vol.

Jason Turuwhenua, Tzu-Ying Yu, Zan Mazharrullah, Benjamin Thompson, "A method for detecting optokinetic nystagmus based on the optic flow of the limbus", Vision Research, vol.

T. Pander, R. Czabanski, T. Przybyla, J. Jezewski, D. Pojda-Wilczek, J. Wrobel, K. Horoba, M. Bernys, A new method of saccadic eye movement detection for optokinetic nystagmu.

Sara T. Wester, Joseph F. Rizzo III, M. David Balkwill, Conrad Wall III, "Optokinetic nystagmus as a measure of visual function in severely visual impaired patients", Investig.

Nicola S. Anstice, Benjamin Thompson, "The measurement of visual acuity in children: an evidence-based update", Clin. Experim, Optometry, vol. 97, No. 1, 2014, pp. 3-11.

Edward J. Engelken, Kenneth W. Stevens, "A new approach to the analysis of nystagmus: An application for order-statistic filter", USAF School of Aerospace Medicine, Clinical S.

Jonathan Waddington, Christopher M. Harris, "Human optokinetic nystagmus: A stochastic analysis", Journal of Vision, (2012) 12(12):5, pp. 1-17.

A. Björck, Numerical methods for least squares problems, Society for Industrial Mathematics, No. 51, 1996.

Keijo Ruohonen, Statistics 1, Tampere University of Technology, 2011.

Erich L. Lehmann and Joseph P. Romano, Testing Statistical Hypotheses, Springer, 2008.

\* cited by examiner

APPARATUS AND METHOD FOR OBJECTIVE VISUAL ACUITY MEASUREMENT USING DYNAMIC VELOCITY THRESHOLD FILTER IN OPTOKINETIC RESPONSE PROCESSING

FIELD OF THE INVENTION

The present invention relates to the field of medical diagnosis and monitoring.

BACKGROUND OF THE INVENTION

Objective measurement of visual acuity is beneficial to the patients who lack cognitive, attentional and language capabilities and can't comply with the test instructions. This is useful in the pre- and postoperative assessment of visually impaired patients or in patients with arresting and preventing disorders such as amblyopia for young children. Optokinetic nystagmus (OKN) is a reflexive eye movement that is induced by movement of objects, such as drifting bars, dots or other shapes on a computer screen, as described in for example [1] Joon Young Hvon, Hwan Eok Yeo, Jong-Mo Seo, In Bun Lee, Jeong-Min Hwang, "Objective measurement of distance visual acuity determined by computerized optokinetic nystagmus test", Investigative Ophthalmology & Visual Science, February 2010, Vol 51, No. 2, pp 752-757; [2] Nikki J. Rubinstein, Larry A. Abel, "Optokinetic nystagmus suppression as index of the Allocation of visual attention", Investigative Ophthalmology & Visual Science, January 2011, Vol. 52, No. 1, pp 462-467; and [3] Mehrdad Sani, Benjamin Thompson, Jason Turuwhenua, "An optokinetic nystagmus detection method for use with young children", IEEE Trans. Engineering in Health and Medicine, Vol 3, 2015.

Subconsciously, a patient's eyes initially rotate to follow moving objects, but beyond a certain point the eyes return to a primary position. The optokinetic response recorded by an eye tracking system therefore consists of an alternating sequence of slow phases (SPs) during which the eyes track a feature of the moving stimulus, and quick phases (QPs) where the eyes move rapidly in the opposite direction to the moving stimulus, see [3] Mehrdad Sani; [4] Jason Turuwhenua, Tzu-Ying Yu, Zan Mazharrullah, Benjamin Thompson, "A method for detecting optokinetic nystagmus based on the optic flow of the limbus", Vision Research, Vol. 103, 2014, pp 75-82; and [5] T. Pander, R. Czabanski, T. Przybyla, J. Jezewski, D. Pojda-Wilczek, J. Wrobel, K. Horoba, M. Bernys, "A new method of saccadic eye movement detection for optokinetic nystagmus analysis", Proc. of 34th Annual International Conference, IEEE EMBS, 2012, pp 3364-3467 (see Figure. 1). The character of the optokinetic response, SPs and QPs, in the eye tracking recording indicates whether or not the patient can see the moving object. By varying the display subject size (e.g. thickness of the bars, diameter of the dots, etc.), luminance contrast, or moving speed, the patient's visual acuity can be assessed, see [1] Joon Young Hyon; [6] Sara T. Wester, Joseph F. Rizzo III, M. David Balkwill, Conrad Wall III, "Optokinetic nystagmus as a measure of visual function in severely visual impaired patients", Investigative Ophthalmology & Visual Science, October 2007, Vol 48, No. 10, pp 4542-4548; and [7] Nicola S. Anstice, Benjamin Thompson, "The measurement of visual acuity in children: an evidence-based update", Clin. Experim, Optometry, Vol. 97, No 1, 2014, pp 3-11.

There are many articles and patents that have revealed and discussed methods on how to identify the slow phases and quick phases in optokinetic responses, such as [3] Mehrdad Sani; [4] Jason Turuwhenua; [5] T. Pander, R. Czabanski; [8] Edward J. Engelken, Kenneth W. Stevens, "A new approach to the analysis of nystagmus: An application for order-statistic filter", USAF School of Aerospace Medicine, Clinical Sciences Division Publication, Oct. 23, 1989; and [9] Jonathan Waddington, Christopher M. Harris, "Human optokinetic nystagmus: A stochastic analysis", Journal of Vision, (2012) 12(12):5, pp 1-17.

Still, optokinetic nystagmus is not widely used clinically in the ophthalmic field, especially for young children's vision diagnosis. The challenge to identify the presence or absence of OKN rests on the fact that the optokinetic responses in a general clinical environment is not ideal as displayed in FIG. 1. There are often involved non-OKN activities such as head movements, spurious eye movements, blinks, and random signal noise during the tests, which may lead to false judgment. A more practical optokinetic response is displayed in FIG. 2. For young children, the additional challenge is to allow unrestrained head movement without wearing a head set.

The conventional approach to identify the SPs or QPs includes a fixed velocity threshold as discussed in [4] Jason Turuwhenua; and [5] T. Pander. The convention approach assumes that the eye QP movement is much faster than the SP movement, therefore, QPs appear as peaks in the eye movement velocity recording as shown as 6 in FIG. 1; The fixed velocity threshold can identify and remove QPs, averaging the remaining data to give a velocity of SPs. However, the noises, spikes and drifts in the OKN response are random and can be significant in comparison with QP peaks. Using a fixed threshold filter often cannot reach a satisfied result.

SUMMARY OF THE INVENTION

The present invention is directed to a design of a system and method for performing an objective and automated optokinetic nystagmus (OKN) testing that can provide a quick and reliable quantitative assessment of patients' visual acuities.

Optokinetic responses typically present sawtooth curve like signals that consist of an alternating sequence of slow phases (SPs) with relatively flat slopes and quick phases (QPs) with steep slopes. By identifying SPs or QPs in optokinetic responses the visibility of the moving stimulus to the patients can be determined. By varying the size, luminance contrast and speed of the stimulus moving objects, the patients' visual acuity can be assessed.

Conventional approach includes a fixed velocity threshold to identify SP response and QP peaks in an OKN response. Often, the response involves random noises, spikes and drifts, which result in an unsatisfied finding.

A dynamic velocity threshold (DVT) filter is introduced in this invention. It applies a set of velocity threshold instead of a fixed one; varies from the minimum threshold to the maximum one; sets a series of restrict conditions to remove possible noises; Uses linear regression, standard deviation and F statistics to find the SP response The advantages of DVT filter are: Using sets of varying velocity thresholds has a better chance to find SP velocity than a fixed threshold; A series of restrict conditions can efficiently remove noises; Using statistical approaches can find a best quantitative estimation for the SP velocity among all the findings.

In at least one embodiment of the present application, an apparatus is provided comprising: a computer processor; a computer monitor; a display device; and a computer memory. The computer processor may be programmed by a computer program stored in the computer memory to: display a plurality of visual stimuli on a screen of the display device for observation by one or two eyes of a patient; record, in the computer memory, a plurality of eye movement signals received from one or two eyes of the patient in response to the plurality of visual stimuli; and display an indication on a screen of the computer monitor of whether one or more reflexive eye movements occur for each of the plurality of eye movement signals. Each of the plurality of eye movement signals may indicate displacement of an eye.

The computer processor may be programmed to determine a plurality of eye movement velocity signals by performing a derivative calculation on each of the plurality of eye movement signals. The computer processor may be programmed to identify one or more slow phase eye movements. and one or more quick phase eye movements. The computer processor may identify a slow phase eye movement if each eye movement velocity signal is within a threshold range for a predetermined number amount of time. The computer processor may identify a quick phase eye movement if each eye movement velocity signal is outside the threshold range for the predetermined amount of time.

The computer processor may be programmed to calculate a linear regression line to fit a set of eye movement signals for each slow phase eye movement identified, so that a plurality of linear regressions lines are calculated for a plurality of slow phase eye movements identified. The computer processor may be programmed to pick the threshold range from among a set of threshold ranges, so that an average deviation between the plurality of linear regression lines and their corresponding set of eye movement signals is less than if any other threshold range from among the set of threshold ranges was used.

In at least one embodiment of the present application, each of the plurality of eye movement signals is based on infrared eye tracking that detects an eye gaze position on the screen of the display device.

The computer processor may be programmed to perform a dynamic velocity threshold filtering process on each of the plurality of eye movement signals to determine if reflexive eye movements occur.

The computer processor may be programmed to determine if a slow phase eye movement is followed by a quick phase abrupt jump of eye movement in an opposite direction to determine if reflexive eye movements occur.

The plurality of visual stimuli may be comprised of images of objects moving horizontally on the screen of the display device. The plurality of visual stimuli may be comprised of first and second sessions; wherein the first session shows a plurality of images of a plurality of objects moving in a first direction at a first speed; and wherein the second session shows the plurality of images of the plurality of objects moving in a second direction, which is opposite the first direction, at the first speed.

In at least one embodiment of the present application, each of the plurality of eye movement signals is based on an electrooculogram that amplifies an electrical signal produced by movement of a particular eye of the patient, detected from two or more electrodes attached to a face of the patient near the particular eye of the patient.

In at least one embodiment of the present application, the computer processor may be programmed to calculate an eye movement slow phase speed by averaging slopes of all of the plurality of linear regression lines of the corresponding plurality of slow phase eye movements identified.

In at least one embodiment of the present application, a method is provided which includes displaying a plurality of visual stimuli on a screen of a display device for observation by one or two eyes of a patient; recording, in a computer memory, a plurality of eye movement signals received from one or two eyes of the patient in response to the plurality of visual stimuli; and displaying an indication on a screen of a computer monitor of whether one or more reflexive eye movements occur for each of the plurality of eye movement signals; wherein each of the plurality of eye movement signals indicates displacement of an eye; and further comprising using a computer processor to determine a plurality of eye movement velocity signals by performing a derivative calculation on each of the plurality of eye movement signals; using the computer processor to identify one or more slow phase eye movements. and one or more a quick phase eye movements; using the computer processor to identify a slow phase eye movement if each eye movement velocity signal is within a threshold range for a predetermined number amount of time; using the computer processor to identify a quick phase eye movement if each eye movement velocity signal is outside the threshold range for the predetermined amount of time; using the computer processor to calculate a linear regression line to fit a set of eye movement signals for each slow phase eye movement identified, so that a plurality of linear regressions lines are calculated for a plurality of slow phase eye movements identified; and using the computer processor to pick the threshold range from among a set of threshold ranges, so that an average deviation between the plurality of linear regression lines and their corresponding set of eye movement signals is less than if any other threshold range from among the set of threshold ranges was used. The method may be consistent with aspects of the apparatus previously specified. In particular the method may include various steps in which a computer processor is used, consistent with aspects of one or more apparatus previously specified.

DETAILED DESCRIPTION OF THE DRAWINGS

Figure 1:
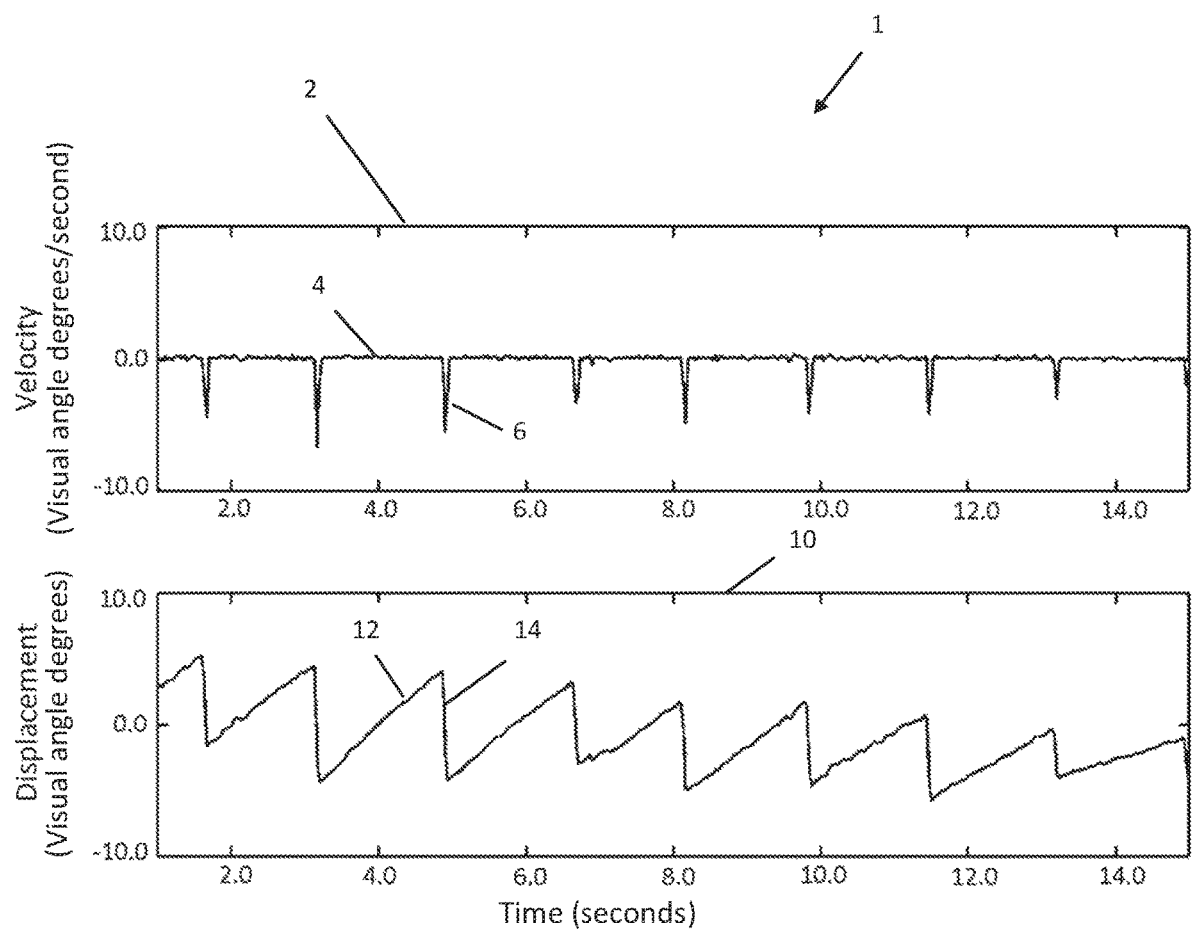
FIG. 1 is a diagram of an ideal optokinetic nystagmus response published in Mehrdad Sani.

FIG. 1 presents a diagram 1 of a known ideal optokinetic nystagmus response. The diagram 1 includes a top plot or section 2 and a bottom plot or section 10. The bottom plot 10 shows the displacement of eye movement, in visual angle degrees versus time in seconds, in reference to a center position of a stimulus screen. The top plot or section 2 shows the velocity of the eye movement in visual angle degrees per second versus time in seconds. Segment 12 represents a slow phase (SP) response and segment 14 of the bottom plot 10 represents a quick phase (QP) response. Their velocities are represented by segment 4 and segment 6 respectively in top plot or section 2. The general parameters of the diagram 1 are known and published in Mehrdad Sani.

Figure 2:
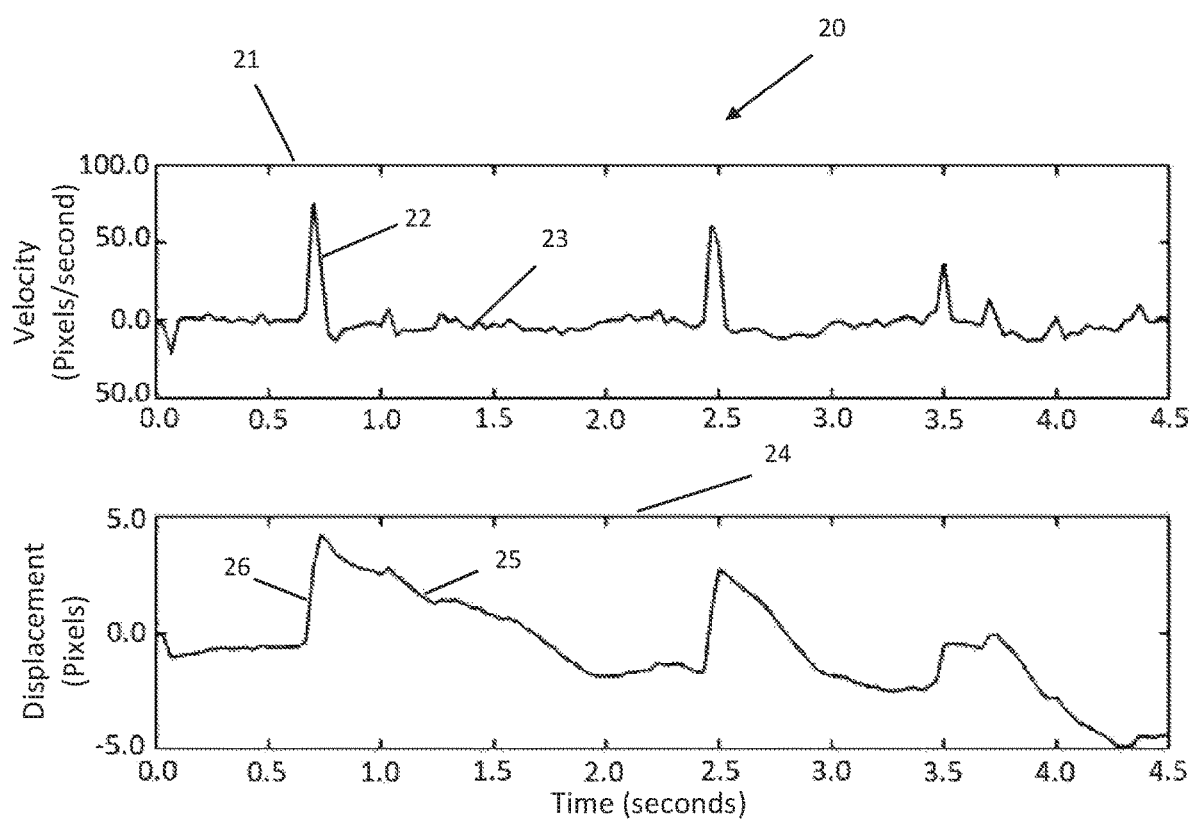
FIG. 2 is diagram of an optokinetic nystagmus response often seen containing noises and drifts published in Mehrdad Sani.

FIG. 2 presents a diagram 20 of a practical optokinetic nystagmus response where more noises and drifts are involved. The diagram 20 includes a top plot or section 21 and a bottom plot or section 24. The bottom plot 24 shows the displacement of eye movement in visual angle degrees versus time in seconds in reference to the center position of the screen of the stimulus display device 33 in FIG. 3. The top plot or section 21 shows the velocity of the eye movement, in visual angle degrees per second versus time in seconds. Segment 25 represents a slow phase (SP) response and segment 26 represents a quick phase (QP) response. Their velocities are represented by segment 23 and segment 22 respectively in top plot or section 21. The general parameters of the diagram 20 are known and is published in Mehrdad Sani.

Figure 3:
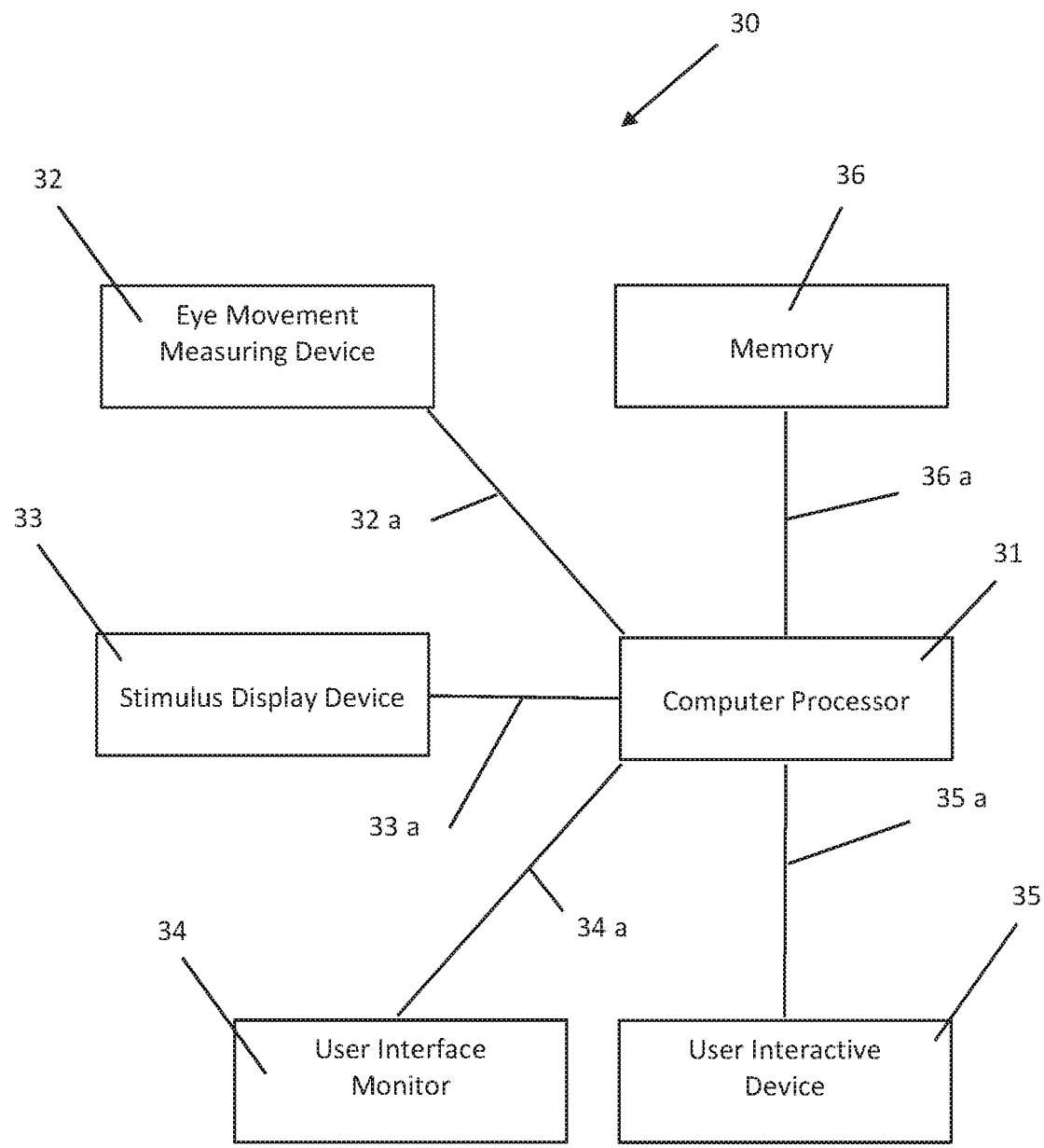
FIG. 3 is a block diagram illustrating the overall architecture of an embodiment of the present invention.

FIG. 3 is a block diagram of a system, method, and apparatus 30 of an overall architecture of an embodiment of the present invention. The system, method, and apparatus 30 includes a computer processor 31, an eye movement measuring device 32, a stimulus display device 33, a user interface monitor 34, an interactive device 35, and a computer memory 36. The interactive device 35 may be a computer mouse and/or a keyboard or other known input device. The memory 36 may be any type of computer memory. The interface monitor 34 may be a typical computer display monitor.

The computer processor 31 may be electrically connected by a communication bus (e.g., PCI (Peripheral Component Interconnect)) 33a to a stimulus display device 33; and by a communication bus (e.g., PCI, USB (Universal Serial Bus), etc.) 32a to an eye movement measuring device 32. The computer processor 31 may be electrically connected by communication lines 34a, 35a, and 36a, to the user interface monitor 34, interactive device 35, and the memory 36, respectively.

The computer processor 31 may be a computer processor for a typical personal computer. The computer processor 31 typically controls the operation of both the eye movement measuring device 32 for data acquisition and the stimulus display device 33 for stimulus display.

The eye movement measuring device 32 typically can be an eye tracking system or an electrooculogram (EOG) acquisition system that includes an amplifier to enhance EOG signals and an A/D (analog to digital) converter to convert the EOG analog signals to digital signals. The eye movement measuring device 32 connects to the computer processor 31 through communication line 32a, typically a USB cable. The details of the eye movement measuring device 32 are described in FIGS. 4 and 5.

The visual stimulus display device 33 typically includes a liquid-crystal display (LCD) or an organic light emitting diode (LED) display monitor and a graphics card, and is connected to and controlled by the computer processor 31 for generating visual stimuli, moving objects, on the display screen of device 33 to be viewed by patients.

Figure 4:
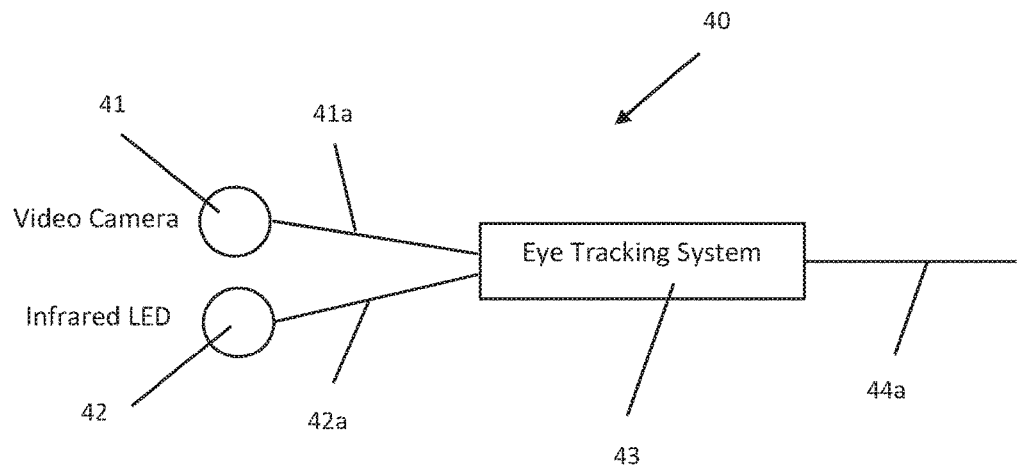
FIG. 4 illustrates a known typical eye tracking system, method, and apparatus.

FIG. 4 shows a typical eye tracking device 40 that is comprised of an eye tracking system 43, one or more infrared LEDs 42 and a video camera 41. Infrared light produced by the light emitting diode (LED) 42 is reflected from the pupil of a person's eye and sensed by a video camera 41. When the person's eye moves, the reflection from the pupil also changes. The eye images collected by the video camera 41 are sent to the eye tracking system 43 via connection 41a for processing. The eye tracking system 43 may include a microprocessor or a controller and memory, in which computer software is stored. By analyzing the video information sent by the camera the eye tracking system 43, by used of computer software programmed in computer memory, can determine the visual angle of the eye movement. Based on the sampling rate of the camera 41, the eye movement velocity can be calculated by the system, apparatus, and method 43, as programmed by computer software stored in computer memory. More information regarding the infrared eye tracking can be found online from Wikipedia (https://en.wikipedia.org/wiki/Eye_tracking). The eye tracking system 43 can control the light emitting diode (LED) 42 ON and OFF via connection line 42a. The eye tracking system sends the eye movement information, angle and speed, to the computer processor 41 in FIG. 3 through connection line 24a, typically a universal serial bus (USB) cable.

Figure 5:
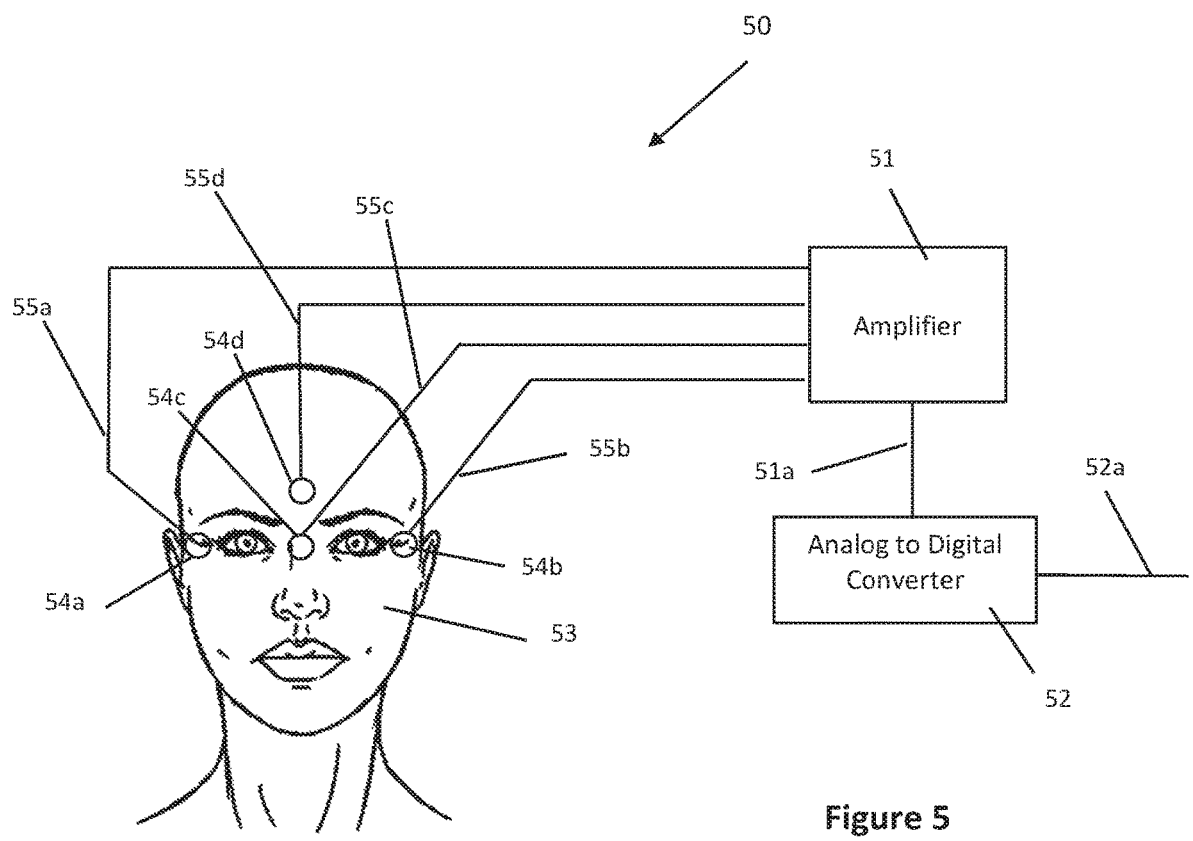
FIG. 5 is a diagram of an electrooculogram (EOG) sensor device.

FIG. 5 shows an electrooculogram (EOG) sensor system, apparatus, and method 50. The apparatus 50 includes an amplifier 51 and an analog-to-digital converter 52. To measure eye movement of the patient 53, there are four skin electrodes attached to the face of the patient 53. Electrodes 54a and 54b are attached to the outer corners of the right and left eyes. The apparatus 50 also includes a reference electrode 54c that attaches to the center between the two eyes of the patient 53. The apparatus 50 also includes a ground electrode 54d that attaches to the forehead of the patient 53. All four electrodes (54a, 54b, 54c, and 54d) are connected to the input of the amplifier 51 by cables 55a, 55b, 55c, and 55d (respectively).

Each eye of the patient 53 is an origin of a steady electric potential field. Each eye's electric potential field can be modelled by a dipole with its positive pole at the cornea and its negative pole at the retina. When an eye of the patient 53 moves, the visual angle changes the voltage across the corners of the eye. Thus, in FIG. 5, electrodes 54a and 54c measure the patient's right eye movement, while electrodes 54b and 54c measure the left eye movement. The voltage changes across the corners of the eyes are sensed and enhanced by the amplifier 51 through electrode cables 55a, 55b, and 55c, and further converted to digital format by ADC (analog to digital converter) 52 through cable 51a. The digital information for the eye movement from the ADC 52 is sent to the computer processor 31 through USB cable 52a in FIG. 5, or component or communications link 32a in FIG. 3. More information regarding generally EOG eye tracking can be found online from Wikipedia (https://en.wikipedia.org/wiki/Eye_tracking#Electric_potential_measurement).

Figure 6:
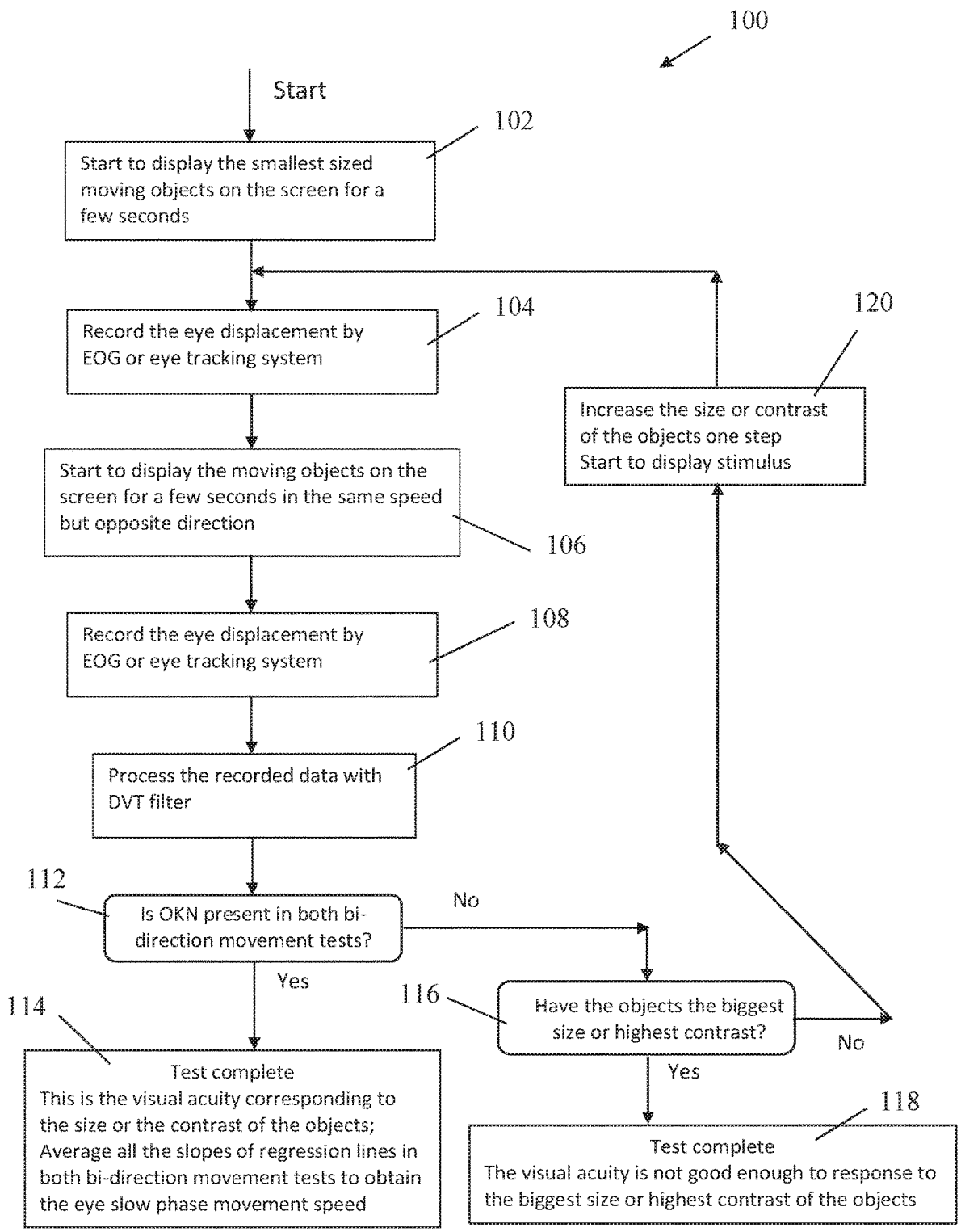
FIG. 6 is a flowchart of visual acuity assessment procedure with objective and automated optokinetic nystagmus (OKN) approach in accordance with an embodiment of the present invention.

FIG. 6 is a flowchart 100 of a visual acuity assessment method or procedure with OKN approach. The method of FIG. 6 starts with step 102 to display the smallest sized moving objects (e.g. dots or vertical lines, etc.) on the screen of the stimulus display device 33 shown in FIG. 3 for a few seconds. In the next step 104 the eye displacement is recorded by EOG approach in FIG. 5 or eye tracking system in FIG. 4, and saved in computer memory 36 in FIG. 3. Step 106 displays the same objects with the same speed but opposite direction on the stimulus display device 33 shown in FIG. 3. Step 108 records the eye displacement by EOG approach or eye tracking system and stores the data in computer memory 36 in FIG. 3. Step 110 processes the eye displacement data saved in computer memory 36 in FIG. 3, using Dynamic Velocity Threshold (DVT) filter of the computer processor 31, as programmed by computer software stored in the computer memory 36, which searches linear regression lines in the eye displacement recording in memory 36; their slopes represent the eye slow phase movement velocity. Step 112 examines if OKN is present in the eye displacement. If OKN is present, the computer processor 31 is programmed by computer software in the computer memory 36 to go to step 114 that averages the slopes of the regression lines generated by DVT to obtain an estimation of eye slow phase movement speed; completes the test and displays the results on monitors or computer monitors 34, and the visual acuity is determined by the size of the objects; If OKN is not present, the computer processor 31 next executes step 116 to check if the objects are the biggest size or the highest contrast. If the objects are the biggest size or the highest contrast, the computer processor 31 is programmed by computer software to next execute step 118 that derives a conclusion that the visual acuity failed to respond to the test; If step 116 finds that the objects are not the biggest size or the highest contrast, the computer processor 31 next executes step 120 that increases the object size or contrast one step, and repeats the procedure starting from 104.

Figure 7:
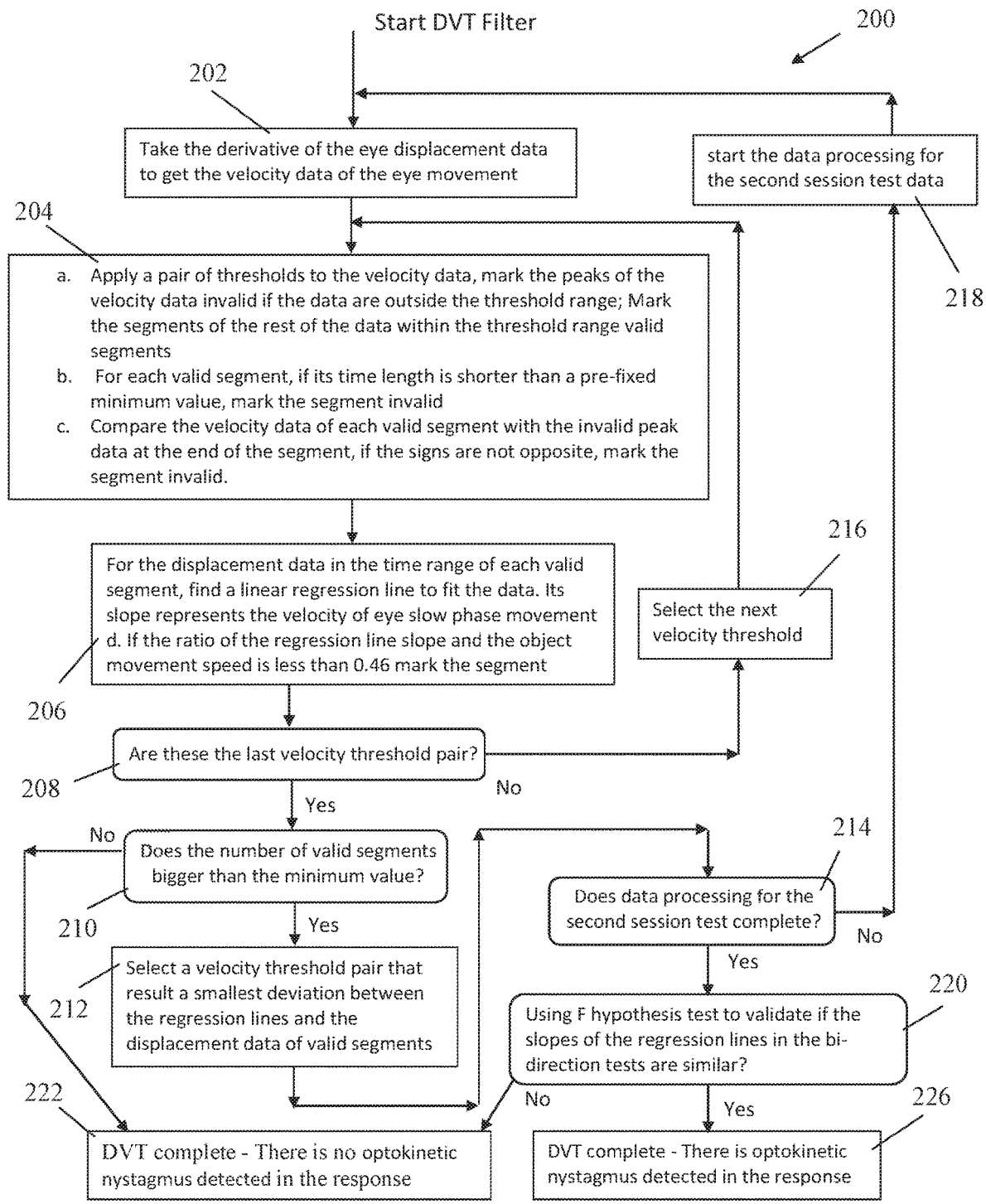
FIG. 7 displays a flowchart for a procedure of a dynamic velocity threshold (DVT) method in accordance with an embodiment of the present invention.

FIG. 7 displays a flow chart 200 of a procedure of a Dynamic Velocity Threshold (DVT) method executed by the computer processor 31, as programmed by computer software stored in computer memory 36 in accordance with an embodiment of the present invention. The method of the chart 200 starts with step 202 at which the computer processor 31 calculates the derivative of the eye displacement data such as data 306 or data 308 shown in the FIG. 8 top plot 302 of the diagram 300, to obtain eye movement velocity, such as velocity data 356 or 358 in the FIG. 8 bottom plot 350.

Starting at step 204, there are four procedures (a.), (b.), (c.) in step 204 and (d.) in step 206, in the diagram of FIG. 7 executed by the computer processor 31 as programmed by computer software stored in the computer memory 36, to filter out invalid data: (a.) Apply a pair of threshold limits to the velocity data (360 or 362 in the bottom plot 350 of FIG. 8); mark the peaks of the velocity data invalid if the data are outside the threshold range; mark the segments of the rest of the data within the threshold range valid segments; (b.) For each valid segment, if the time length is shorter than a pre-fixed minimum value (e.g. 0.2 second), mark the segment invalid; (c.) Since the slow phase movement and the quick phase movement move in opposite direction, compare the velocity data of each valid segment (slow phase) with the invalid peak data at the end of the segment (quick phase). If the signs are not opposite, mark the segment invalid, in computer memory 36.

Figure 9:
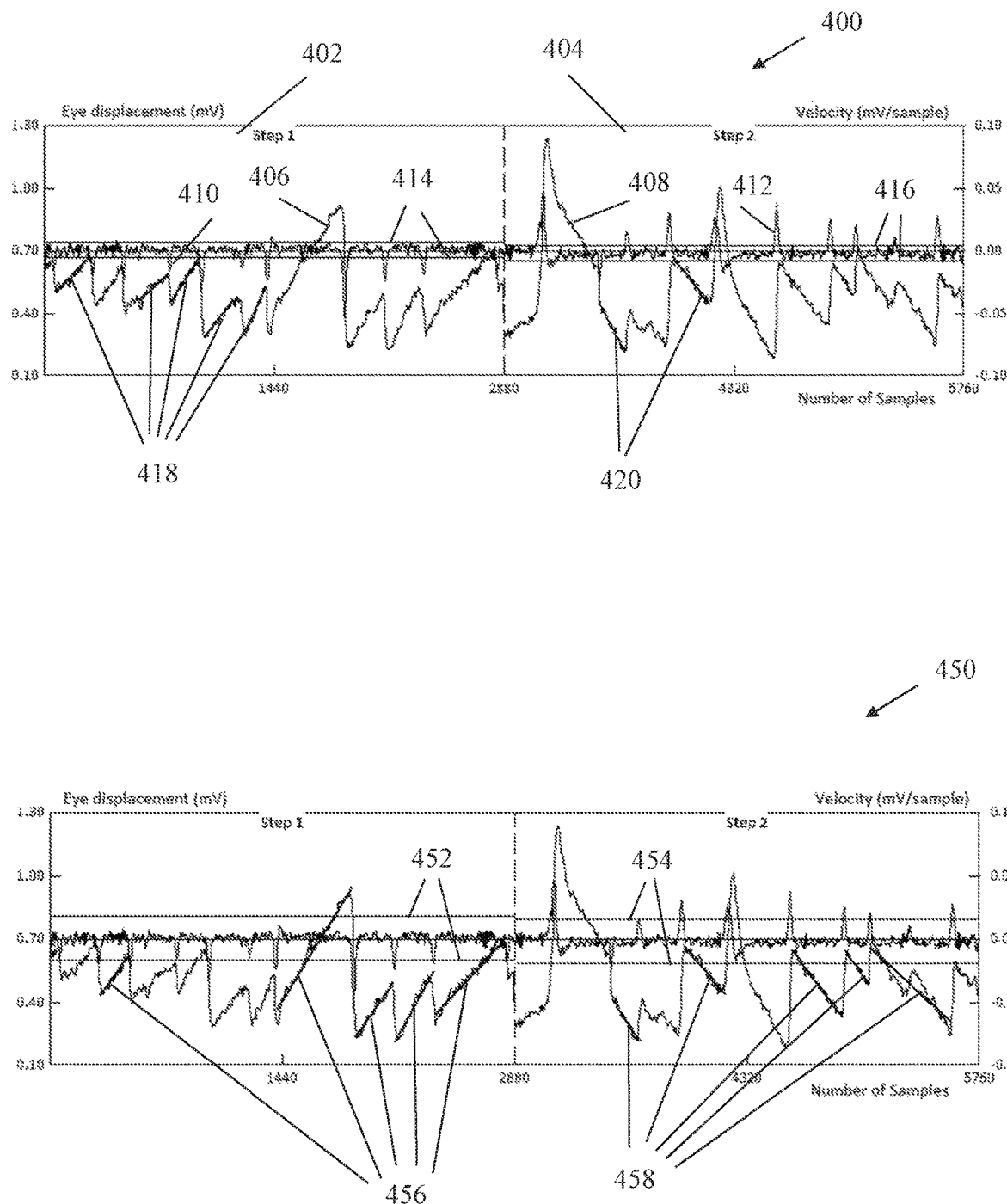
FIG. 9 displays the same objective and automated optokinetic nystagmus (OKN) response as in FIG. 8 and two different levels of velocity thresholds which yield two different sets of linear regression lines and eye movement velocities.

At step 206, for each segment of valid data the computer processor 31 is programmed by computer software to calculate linear regression lines to fit the slow phase data in the valid segments as displayed as 418 and 420 in FIG. 9 top plot 400 and data 456 and 458 in FIG. 9 bottom plot 450. At the filtering process d in step 206, as disclosed in the reference to Sara T. Wester, if the ratio of the regression line slope and the object movement speed is less than 0.46 the segment is marked invalid in computer memory 36 by the computer processor 31 as programmed by computer software.

At step 208, the computer processor 31, as programmed by computer software stored in the computer memory 36, checks if the threshold pair is the last one in the set, stored in computer memory 36. If it is not, the next pair of thresholds is selected by the computer processor 31 at step 216 and the computer processor 31 moves causes a loop back to step 204; if the pair of thresholds is the last pair in the set stored in computer memory 36, then the computer processor 31 is programmed to move to step 210 to check if any number of valid segments stored in computer memory 36 for any pair of thresholds is bigger than a prefixed minimum value stored in computer memory 36. If there is no number of valid segments bigger than the prefixed minimum value, which means OKN is not detected for any pair of thresholds stored in computer memory 36, the DVT method completes at step 222 and yields a conclusion, which is stored by the computer processor 31 into computer memory 36, that there is no OKN detected; if there is a number of valid segments for any pair of thresholds is bigger than the prefixed minimum value the computer processor 31 is programmed to make a decision that OKN is detected, the computer processor next executes step 212.

At step 212, the computer processor 31 is programmed to select a pair of velocity thresholds based on two conditions: i) The number of valid segments bigger than a minimum value; ii) the smallest deviation between the regression lines and the displacement data of valid segments.

At step 214, the computer processor 31 checks if the second session data have been processed. If the second session data have not been processed, the computer processor 31 is programmed to start data processing for the second session test data with opposite direction movement at step 218. If the data of the second session test is complete, the computer processor 31 is programmed to next execute step 220 to validate, using F hypothesis test as described in DVT procedure (10) below, if the velocities calculated by the computer processor 31 in the two session tests are identical. A conclusion is given there is OKN response in the test if the velocities in the two sessions are identical, or there is no OKN response if the velocities in the two sessions are not identical.

Figure 8:
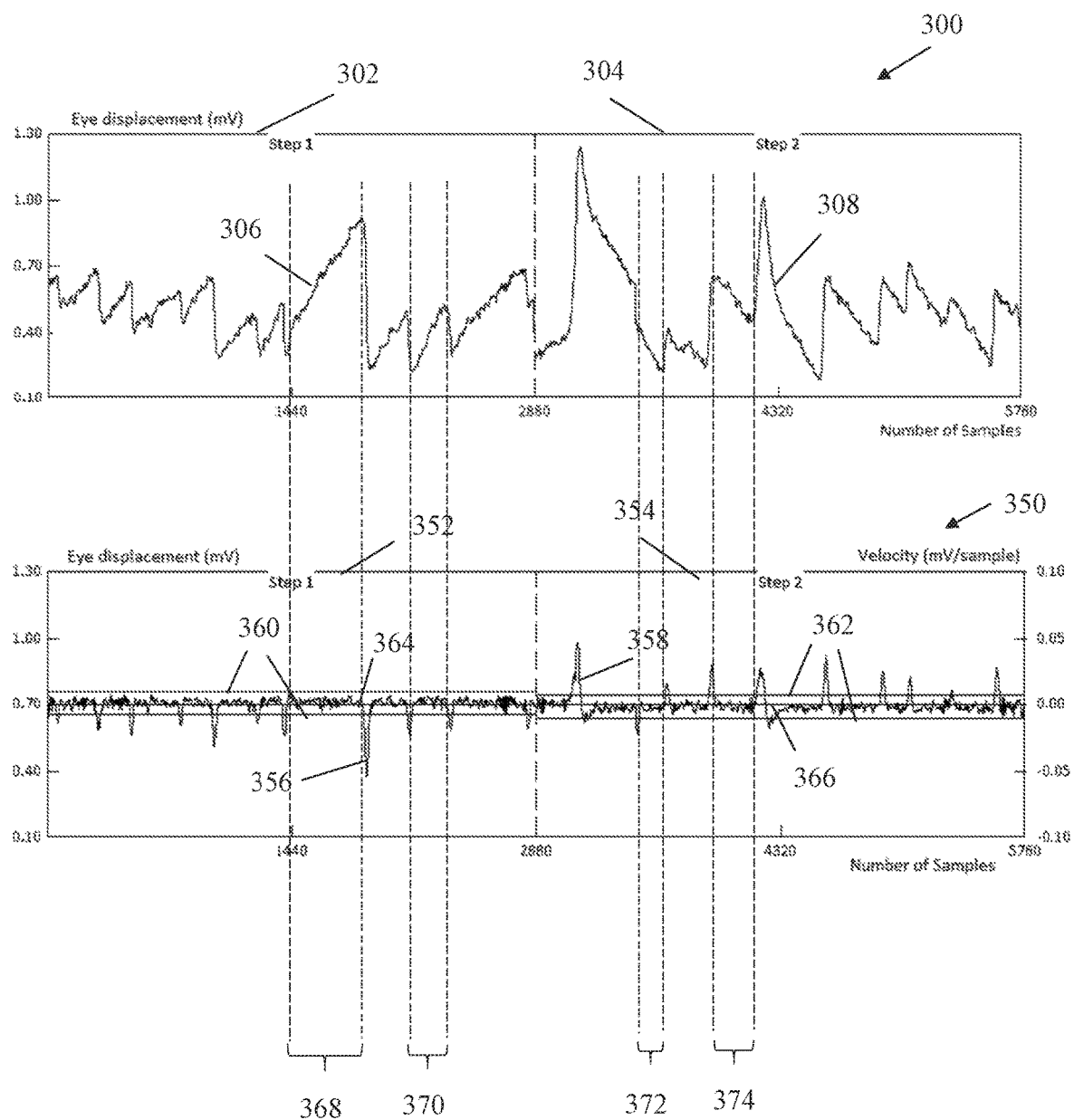
FIG. 8 illustrates an objective and automated optokinetic nystagmus (OKN) response and a range of velocity thresholds from test data of an embodiment of the present invention.

FIG. 8 displays a diagram of OKN test results. The top plot 300 is eye displacement in millivolts (mV) that can be converted to inches as described below versus time in number of samples that can be converted to seconds as described below, the bottom plot 350 is eye movement velocity versus time. Two sessions are included in the test. The stimulus objects move in the same speed but different direction in each session. A plot 302 of eye displacement in the first session is shown in FIG. 8. A plot 304 of eye displacement in the second session is also shown in FIG. 8. Displacement responses 306 and 308 in the first session and the second session, respectively, are also shown in FIG. 8.

Plot 352 of eye velocity in millivolts per sample in the first session and plot 354 of eye velocity in millivolts per sample in the second session are also shown in FIG. 8. Eye velocity responses 356 and 358 in the first session and the second session, respectively, are also shown in FIG. 8.

The electrooculogram approach is typically used for the test. A 20.5 inch wide liquid crystal display (LCD) monitor and/or computer monitor is used to display the stimulus on the monitor. The displacement unit is measured as microvolt that can be converted to percentage of screen width by a factor of 1.75. That is, microvolt×1.75=percentage of 20.5 inches.

The time scale is in the unit of number of samples. It can be converted to seconds by the sampling rate which is 600 Hz. That is, Number of samples/600=seconds.

Screen object movement speeds 364 and 366 in the first session and in the second session have been converted to microvolts by the same factor microvolt/(number of samples)=percentage of 20.5 inches/Number of samples/1.75.

Velocity thresholds 360 and 362 in the first session and in the second session are shown in FIG. 8. Assume the screen object movement speed is v, threshold is vt, the threshold pair are v+vt and v−vt. By applying proper level of threshold to filter, by use of computer processor 31, out the velocity data outside threshold range, the quick phase (QP) peaks can be detected.

The segments containing data within the threshold limit are valid segments. As examples, the time ranges 368, 370, 372, and 374 are valid segments. Data in these segments are within the threshold limit.

FIG. 9 demonstrates that by applying different levels of velocity thresholds, different slow phase movements may be detected. Two sessions are included in the test. The stimulus objects move in the same speed but different direction in each session. The plot 400 shown in FIG. 9 is for both session tests including eye displacement, velocity, velocity thresholds and linear regression lines for the displacement responses. Plot 402 is for the first session and plot 404 is a plot for the second session. Eye displacement data 406 and 408 are also shown in FIG. 9. Eye velocity data 410 and 412 are also shown in FIG. 9. Velocity threshold pairs 414 and 416 are also shown in FIG. 9. linear regression lines 418 and 410 for the eye displacement responses 406 and 408 in valid segments are also shown in FIG. 9. The slopes of the linear regression lines represent the velocity of eye slow phase movement.

Plot 450 is also shown in FIG. 9 and is a similar to plot 400 except there is a different level of velocity thresholds applied. Pairs of velocity thresholds 452 and 454 are also shown in FIG. 9. The ranges of the thresholds are much bigger than the ranges of the thresholds 414 and 416 in the top plot 400 of FIG. 9. Linear regression lines 456 and 458 fit the eye displacement response in the valid segments. The linear regression lines 456 and 458 are considerably different from the linear regression lines 418 and 420 in the top plot 400 of FIG. 9.

In one or more embodiments of the present invention, a system, method, and apparatus are configured with the following considerations: (1.) the measurements should be as robust, quick and accurate as possible to suit the rapid clinical test environment; and (2.) the filter should be sophisticated enough to practically remove the noises and artifacts and identify the true SPs and QPs responses under general test conditions.

A dynamic velocity threshold (DVT) technique is provided in at least one embodiment of the present invention. It uses a set of velocity thresholds instead of a fixed one; varies from the minimum threshold to the maximum one; collects sets of SP velocities calculated based on the set of thresholds; It further uses several restrictions to remove some signals that are most likely noises and do not belong to the part of the SP responses; It compares the sets of SP velocities collected, and picks the set that has the best linear regression fitting to the SP velocities.

The advantages of DVT filter are: (1.) using sets of varying velocity thresholds has a much better chance to find SP velocity than a fixed threshold if the SP response exits in the data recorded; and (2.) although using multiple velocity threads has more chances of searching for SP responses than a single fixed thread, by carefully setting the restrict conditions as indicated by steps 204 and 206 in FIG. 7, the DVT filter will not have more chances than the fixed threshold approach to falsely identify a noise as a SP response if SP response doesn't exist; and (3.) the set of calculated SPs that has the best linear regression fitting has a greater likelihood of reflecting the true value or accurate estimation of the SP movement velocity than the fixed threshold can produce.

An OKN test system architecture in at least one embodiment of the present invention is illustrated in FIG. 3. The visual stimulus is controlled by a computer system to display moving subjects. The pattern, luminance, contrast, size of the subjects, moving speed and direction, and display duration are the parameters configured by the user. Generally, the smaller the object size, the quicker the moving speed, the lower the object contrast visible to a patient, the higher visual acuity the patient will have. The whole test procedure can start with the lowest visibility level. If the patient fails to generate optokinetic response, the visibility level can be gradually increased. This procedure can be controlled manually or by a computer program automatically. It is a good practice to display a cartoon image or animation at the center of the screen to get the patient's attention first. Once the patient's gaze is detected at the center of the screen, the cartoon image will disappear, and the subjects, vertical bars or random dots, can start moving horizontally on the screen.

A test run may typically be comprised of a pair of sessions. In each session, the subjects on the screen always move in the same speed but in the opposite direction. After calibration, the visual angle of eye movement in reference to the center or the edge of the screen can be measured by an eye tracking system or an electrooculography (EOG) system displayed in FIG. 4 and FIG. 5, respectively. Once a run is complete, the computer system immediately processes the data recorded and dynamic velocity threshold (DVT) filter is applied to determine whether optokinetic responses are present. The result is displayed on a user interface monitor and/or computer monitor, and then, the user or the computer program (if it is set to automatic testing mode) can decide how to proceed based on the result. FIG. 6 demonstrates a flowchart of a test procedure for visual acuity assessment, and FIG. 7 demonstrates a flowchart of a DVT filter.

The DVT filter method in accordance with one or more embodiments of the present invention, executed by a computer processor 31, as programmed by computer software stored in computer memory 36, containing steps of data processing procedures, is described as follows:

(1.) Taking the derivative of the eye displacement recording as displayed 306 and 308 in the top plot 300 of FIG. 8 to obtain the velocity of the eye movement as displayed by 356 and 358 in the FIG. 8 bottom plot 350.

(2.) Apply a maximum/minimum velocity threshold preconfigured. Only the velocity data within the limit boundary will be processed as shown in the bottom plot 350 of FIG. 8. As an example, if the screen subject movement speed is v (364, 366 in FIG. 8), the velocity threshold is vt, then, any data with its velocity outside range v+vt and v−vt, as indicated by 360 and 362 in FIG. 8, will be filtered. The assumption is that (a) the eye movement speed is as same as or close to the speed of the objects moving on the screen, and (b) the quick phase responses (QPs) in OKN are presented as peaks in the velocity signal in which by applying velocity thresholds, the QPs can be detected and removed; and (c) The remaining segments in the velocity signal are considered the slow phase (SP) of the eye movement. The SP speed is assumed as a constant with random noise as small variations which can be resolved using the standard least square approach disclosed in [10] A. Björck, Numerical methods for least squares problems, Society for Industrial Mathematics, No. 51, 1996.

(3.) Compare the time length of each segment of data remaining with a preset minimum period. If the time length is less than the minimum period (e.g. a quarter second), the segment will be marked as invalid, and stored in computer memory 36, and hence, not be processed further.

(4.) Assuming the SP responses are located in the valid segments, the QP peaks must occur at the end of each valid segment and the sign of peaks are opposite to the sign of the SP velocities because the SPs and QPs are eye movement in opposite directions. For any valid segment, if the peak at the end has the same sign as the velocity within the segment, the segment will be marked as invalid by the computer processor 31, in computer memory 36.

(5.) For the remaining valid segments, the computer processor 31 uses a linear regression method to obtain straight lines that best fit the displacement data in the valid segments (418, 420, 456, 458 in FIG. 9). The slopes of the regression lines represent the eye slow phase movement velocity.

(6.) The computer processor 31 compares the slopes of the linear regression lines (the SP velocities) with the object's moving speed. As disclosed in [6] Sara T. Wester, if the ratio is less than 0.46, the SP velocity is unrealistically slow, hence, the segment will be marked as invalid by the computer processor 31 in computer memory 36. The criteria of steps (2.), (3.), (4.), and (6.) above are restrict conditions that are designed to efficiently remove noise.

(7.) The computer processor 31 changes the velocity threshold in step (2.) according to a set of preconfigured values (vt1, vt2, vtn), and repeats the procedures (2.)-(6.) to get a set of linear regression lines and slopes in terms of each velocity threshold. As shown in FIG. 9, when the velocity threshold changes, the segments of valid data also change, and so do the slopes of the linear regression lines.

(8.) The computer processor 31 selects a threshold that produces the number of valid segments bigger than a predetermined minimum value, and a minimum standard deviation between the velocity data in the valid segments and the linear regression lines that fit the velocity data. Up to now, we have selected a velocity threshold that results a satisfied number of valid segments and regression lines that best fit the SP responses within the valid segments. Averaging the slopes of the linear regression lines gives an estimation of the slow phase velocity of the eye movement in the optokinetic responses.

(9.) The computer processor 31 constructs and performs the second session test, and repeats the same procedures (1.)-(8.) for processing the second session data. In the first session, the objects on the screen move in one direction, and in the second session the objects move in the opposite direction but with the same speed. The eye following the moving objects in the two sessions should have the same velocity but different signs. Hence, if a velocity measured in the first session is identical to a velocity measured in the second session disregarding the direction, the presence of the slow phase is recognized.

(10.) Assuming the eye movement velocities in the two sessions are identical as [6] Sara T. Wester indicates, the final step is to validate the similarity of the velocities found in the two sessions using F hypothesis test discussed in [11] Keijo Ruohonen, Statistics 1, Tampere University of Technology, 2011; and in [12] Erich L. Lehmann and Joseph P. Romano, Testing Statistical Hypotheses, Springer, 2008; assuming that the two velocities in the two session data are not similar, calculate the F values based on the two session data and the velocities found, and compare the F value with a threshold in the F statistic table of a particular p value. Say p=0.05, if the F value is smaller than the F threshold value, the hypothesis is rejected. Therefore, there is 95% confidence that the two velocities of the eye movement in the two sessions are similar. Otherwise, the hypothesis holds, there is no sufficient confidence that the two velocities are similar.

(11.) Averaging the slopes in the two sessions gives a final estimation of the eye movement velocity.

The DVT filter in accordance with an embodiment of the present invention, executed by the computer processor 31, in accordance with computer software stored in the computer memory 36, includes the above procedures (2.)-(10.) Any result that doesn't satisfy the criteria of the steps (2.)-(10.) above, will lead to a conclusion of unidentifiable optokinetic responses. The rationale of the approach relies on the consideration that the noise involved in the two independent run sessions is random and need a different level of thresholds to properly remove them. It is a practical measure to determine whether an optokinetic response exists in the two run sessions by applying all possible velocity thresholds for filtering.

Another advantage of the DVT filter method and apparatus of one or more embodiments of the present invention, is that, using a statistical method, the computer processor 31 can find regression lines that best fit the velocity of the eye movement in optokinetic responses in a relatively short testing time, which minimize the noises, such as head movement, eye blink and, or spurious eye movements that may be introduced during the test.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. An apparatus comprising:
   a computer processor;
   a computer monitor;
   a display device;
   and
   a computer memory;
   wherein the computer processor is programmed by a computer program stored in the computer memory to:
   display a plurality of visual stimuli on a screen of the display device for observation by one or two eyes of a patient;
   record, in the computer memory, a plurality of eye movement signals received from one or two eyes of the patient in response to the plurality of visual stimuli; and
   display an indication on a screen of the computer monitor of whether one or more reflexive eye movements occur for each of the plurality of eye movement signals;
   wherein each of the plurality of eye movement signals indicates displacement of an eye;

wherein the computer processor is programmed to determine a plurality of eye movement velocity signals by performing a derivative calculation on each of the plurality of eye movement signals;

wherein the computer processor is programmed to identify one or more slow phase eye movements, and one or more quick phase eye movements;

wherein the computer processor identifies a slow phase eye movement if each eye movement velocity signal is within a threshold range for a predetermined number amount of time;

wherein the computer processor identifies a quick phase eye movement if each eye movement velocity signal is outside the threshold range for the predetermined amount of time;

wherein the computer processor is programmed to calculate a linear regression line to fit a set of eye movement signals for each slow phase eye movement identified, so that a plurality of linear regressions lines are calculated for a plurality of slow phase eye movements identified;

wherein the computer processor is programmed to pick the threshold range from among a set of threshold ranges, so that an average deviation between the plurality of linear regression lines and their corresponding set of eye movement signals is less than if any other threshold range from among the set of threshold ranges was used.

2. The apparatus of claim 1 wherein
each of the plurality of eye movement signals is based on infrared eye tracking that detects an eye gaze position on the screen of the display device.

3. The apparatus of claim 1 wherein
the computer processor is programmed to perform a dynamic velocity threshold filtering process on each of the plurality of eye movement signals to determine if reflexive eye movements occur.

4. The apparatus of claim 1 wherein
the computer processor is programmed to determine if a slow phase eye movement is followed by a quick phase abrupt jump of eye movement in an opposite direction to determine if reflexive eye movements occur.

5. The apparatus of claim 1 wherein
the plurality of visual stimuli is comprised of images of objects moving horizontally on the screen of the display device.

6. The apparatus of claim 1 wherein
the plurality of visual stimuli is comprised of first and second sessions;
wherein the first session shows a plurality of images of a plurality of objects moving in a first direction at a first speed; and
wherein the second session shows the plurality of images of the plurality of objects moving in a second direction, which is opposite the first direction, at the first speed.

7. The apparatus of claim 1 wherein
each of the plurality of eye movement signals is based on an electrooculogram that amplifies an electrical signal produced by movement of a particular eye of the patient, detected from two or more electrodes attached to a face of the patient near the particular eye of the patient.

8. The apparatus of claim 1 wherein
the computer processor is programmed to calculate an eye movement slow phase speed by averaging slopes of all of the plurality of linear regression lines of the corresponding plurality of slow phase eye movements identified.

9. A method comprising:
displaying a plurality of visual stimuli on a screen of a display device for observation by one or two eyes of a patient;
recording, in a computer memory, a plurality of eye movement signals received from one or two eyes of the patient in response to the plurality of visual stimuli; and
displaying an indication on a screen of a computer monitor of whether one or more reflexive eye movements occur for each of the plurality of eye movement signals;
wherein each of the plurality of eye movement signals indicates displacement of an eye;
further comprising using a computer processor to determine a plurality of eye movement velocity signals by performing a derivative calculation on each of the plurality of eye movement signals;
using the computer processor to identify one or more slow phase eye movements, and one or more quick phase eye movements;
using the computer processor to identify a slow phase eye movement if each eye movement velocity signal is within a threshold range for a predetermined number amount of time;
using the computer processor to identify a quick phase eye movement if each eye movement velocity signal is outside the threshold range for the predetermined amount of time;
using the computer processor to calculate a linear regression line to fit a set of eye movement signals for each slow phase eye movement identified, so that a plurality of linear regressions lines are calculated for a plurality of slow phase eye movements identified; and
using the computer processor to pick the threshold range from among a set of threshold ranges, so that an average deviation between the plurality of linear regression lines and their corresponding set of eye movement signals is less than if any other threshold range from among the set of threshold ranges was used.

10. The method of claim 9 wherein
each of the plurality of eye movement signals is based on infrared eye tracking that detects an eye gaze position on the screen of the display device.

11. The method apparatus of claim 9 further comprising
using the computer processor to perform a dynamic velocity threshold filtering process on each of the plurality of eye movement signals to determine if reflexive eye movements occur.

12. The method of claim 9 further comprising
using computer processor to determine if a slow phase eye movement is followed by a quick phase abrupt jump of eye movement in an opposite direction to determine if reflexive eye movements occur.

13. The method of claim 9 wherein
the plurality of visual stimuli is comprised of images of objects moving horizontally on the screen of the display device.

14. The method of claim 9 wherein
the plurality of visual stimuli is comprised of first and second sessions;
wherein the first session shows a plurality of images of a plurality of objects moving in a first direction at a first speed; and wherein the second session shows the plurality of images of the plurality of objects moving in a second direction, which is opposite the first direction, at the first speed.

15. The method of claim 9 wherein each of the plurality of eye movement signals is based on an electrooculogram that amplifies an electrical signal produced by movement of a particular eye of the patient, detected from two or more electrodes attached to a face of the patient near the particular eye of the patient.

16. The method of claim 9 further comprising using the computer processor to calculate an eye movement slow phase speed by averaging slopes of all of the plurality of linear regression lines of the corresponding plurality of slow phase eye movements identified.

* * * * *